United States Patent
Stoyanov et al.

(10) Patent No.: US 12,064,087 B2
(45) Date of Patent: Aug. 20, 2024

(54) APPARATUS AND METHOD FOR CAPSULE ENDOSCOPY

(71) Applicant: UCL Business LTD., London (GB)

(72) Inventors: Danail Stoyanov, London (GB); Agostino Stilli, London (GB)

(73) Assignee: UCL Business LTD., London (GB)

( * ) Notice: Subject to any disclaimer, the term of this patent is extended or adjusted under 35 U.S.C. 154(b) by 601 days.

(21) Appl. No.: 17/205,941

(22) Filed: Mar. 18, 2021

(65) Prior Publication Data
US 2021/0204801 A1 Jul. 8, 2021

Related U.S. Application Data

(63) Continuation of application No. PCT/GB2019/052640, filed on Sep. 19, 2019.

(30) Foreign Application Priority Data

Sep. 19, 2018 (GB) .................................. 1815267

(51) Int. Cl.
*A61B 1/04* (2006.01)
*A61B 1/00* (2006.01)

(52) U.S. Cl.
CPC .......... *A61B 1/041* (2013.01); *A61B 1/00027* (2013.01); *A61B 1/00112* (2013.01); *A61B 1/00156* (2013.01); *A61B 2562/0247* (2013.01)

(58) Field of Classification Search
CPC ............................................. A61B 2562/0247
See application file for complete search history.

(56) References Cited

U.S. PATENT DOCUMENTS

| | | | |
|---|---|---|---|
| 2005/0154278 A1* | 7/2005 | Cabiri | A61B 1/04 600/407 |
| 2006/0261771 A1* | 11/2006 | Anhalt | B25J 9/065 318/568.12 |
| 2006/0270901 A1* | 11/2006 | Bern | A61B 1/0016 600/101 |
| 2007/0010709 A1* | 1/2007 | Reinschke | A61B 5/062 600/116 |
| 2007/0197868 A1* | 8/2007 | Takada | A61B 1/31 600/101 |
| 2008/0234546 A1* | 9/2008 | Kawano | A61B 1/00082 600/104 |
| 2009/0227838 A1* | 9/2009 | Allen | A61B 1/00151 600/114 |

(Continued)

FOREIGN PATENT DOCUMENTS

| | | | |
|---|---|---|---|
| JP | 2012191980 A | * 10/2012 | ......... A61B 1/00135 |
| WO | WO 2007/050370 | 5/2007 | |
| WO | WO 2020/058719 | 3/2020 | |

*Primary Examiner* — John P Leubecker
(74) *Attorney, Agent, or Firm* — Levine Bagade Han LLP

(57) ABSTRACT

An apparatus for capsule endoscopy, the apparatus comprising a capsule that comprises: at least one inflatable bladder configured to form a toroid having a hole and an outer periphery when inflated; a plurality of continuous tracks, each extending through the hole and around the outer periphery of the at least one inflatable bladder; and a propulsion system configured to drive the continuous tracks; wherein the capsule is configured such that the continuous tracks slip over the at least one inflatable bladder when driven by the propulsion system.

19 Claims, 4 Drawing Sheets

(56) References Cited

U.S. PATENT DOCUMENTS

| | | |
|---|---|---|
| 2009/0233747 A1* | 9/2009 | Sheridan .............. F16H 37/065 |
| | | 180/9.1 |
| 2009/0275800 A1* | 11/2009 | Zeiner ................. A61B 1/2736 |
| | | 600/115 |
| 2011/0065988 A1* | 3/2011 | Eidenschink ......... A61B 1/267 |
| | | 600/115 |
| 2012/0271106 A1 | 10/2012 | Yamakawa et al. |
| 2012/0271107 A1 | 10/2012 | Yamakawa et al. |
| 2014/0336455 A1 | 11/2014 | Massicotte |
| 2015/0297060 A1 | 10/2015 | Bern |

\* cited by examiner

APPARATUS AND METHOD FOR CAPSULE ENDOSCOPY

CROSS-REFERENCE TO RELATED APPLICATIONS

This application is a continuation of International Patent Application Number PCT/GB2019/052640 filed Sep. 19, 2019, which claims the benefit of priority to GB 1815267.8 filed Sep. 19, 2018, the contents of which are incorporated herein by reference in their entireties.

BACKGROUND

This invention relates generally to endoscopy, for example for imaging the interior of the gastrointestinal (GI) tract. More particularly the present invention relates to an apparatus for capsule endoscopy and a method of capsule endoscopy.

An endoscope can be used to image the interior of a tube. For example, an endoscope can be used for optical screening of the upper and lower human GI tract. A capsule endoscope can include an integrated camera and be small enough for swallowing, passing through and imaging the GI tract.

Passive capsules rely on the peristaltic movements of the GI tract. Therefore, they do not allow for any control on the data collection.

WO 2007/050370 A2 discloses a self-propellable endoscopic apparatus. The apparatus comprises a toroid that defines a central cavity having an interior volume and presenting an exterior surface and an interior surface which move continuously in opposite directions when the apparatus is in motion. A support structure is located within the interior volume of the toroid. A housing structure is located concentrically and coaxially relative to the support structure and disposed in the central cavity of the toroid. Interlocking rollers located on the support and housing structures maintain the two structures in a fixed spatial relationship. A power source connected to the rollers provides a motive force to the toroid.

The morphology of the GI tract significantly changes from the oral cavity to the anus, both in terms of stiffness and diameter. If the endoscopic apparatus is too big for the tract, then there is a possibility that it could get stuck or cause damage to the tract. If the endoscopic apparatus is too small, then it is more difficult to control the movement of the endoscopic apparatus. Some polyps can be hidden in wrinkles of the tract. It can be difficult to find and image these polyps using known endoscopic apparatuses.

It is desirable to provide an apparatus and method for capsule endoscopy that is suitable for the whole of the GI tract (even as its morphology changes) and that is better at finding hidden polyps.

SUMMARY

The present invention attempts to address this desire by providing an apparatus for capsule endoscopy and a method of capsule endoscopy.

According to the invention there is provided an apparatus for capsule endoscopy, the apparatus comprising a capsule that comprises at least one inflatable bladder configured to form a toroid having a hole and an outer periphery when inflated; a plurality of continuous tracks, each extending through the hole and around the outer periphery of the at least one inflatable bladder; and a propulsion system configured to drive the continuous tracks; wherein the capsule is configured such that the continuous tracks slip over the at least one inflatable bladder when driven by the propulsion system.

The capsule may comprise at least one valve corresponding to the at least one inflatable bladder and configured to receive and expel fluid for inflating and deflating the bladder. The apparatus may comprise a controller configured to control an inflation level of the at least one inflatable bladder.

The apparatus may comprise at least one pressure sensor configured to measure a pressure in the at least one inflatable bladder. The at least one pressure sensor may be configured to provide information about the measured pressure to the controller, and the controller may be configured to control the inflation level based at least partly on the information from the at least one pressure sensor.

The continuous tracks may be elastic such that they remain taut around the at least one inflatable bladder over a range of inflation levels of the at least one inflatable bladder.

The capsule may comprise a housing for supporting at least part of the propulsion system, wherein an inner periphery of the toroid that defines the hole is fixed relative to the housing. The apparatus may comprise at least one rigid collar configured to constrain the continuous tracks from moving circumferentially with respect to the hole formed by the at least one inflatable bladder.

The propulsion system may be configured to drive a selectable subset of the continuous tracks. The apparatus may comprise at least two inflatable bladders, wherein the continuous tracks extend between the at least two inflatable bladders.

The apparatus may comprise at least two of said capsule, wherein the at least two capsules and connected end-to-end by a flexible connector.

The apparatus may comprise at least one imaging device for imaging surroundings of the apparatus.

The capsule may be self-propelled. The capsule may comprise a tank of fluid stored in the capsule, wherein the tank is in controllable fluid communication with the at least one inflatable bladder for inflating the at least one inflatable bladder. The capsule may comprise a power supply for supplying power to the propulsion system. When the apparatus comprises at least one imaging device, the power supply may be configured to supply power to the at least one imaging device. When the apparatus comprises a controller, the power supply may be configured to supply power to the controller.

The apparatus may comprise at least one tether for supplying power and/or fluid to the capsule. The apparatus may comprise a power supply for supplying power to the propulsion system and/or a fluid supply for supplying fluid to the at least one inflatable bladder via the at least one tether.

According to the invention there is provided a method of capsule endoscopy, the method comprising: providing in a lumen an apparatus comprising a capsule that comprises: at least one inflatable bladder configured to form a toroid having a hole and an outer periphery when inflated; a plurality of continuous tracks, each extending through the hole and around the outer periphery of the at least one inflatable bladder; and a propulsion system configured to drive the continuous tracks; and driving the continuous tracks with the propulsion system such that the continuous tracks slip over the at least one inflatable bladder and the capsule moves along the lumen.

The method may comprise: inflating and/or deflating the at least one inflatable bladder to an inflation level such that the continuous tracks press against a wall defining the lumen. The method may comprise: measuring a pressure in the at least one inflatable bladder; and controlling the inflation level based at least partly on the measured pressure. Inflating the at least one inflatable bladder may comprise supplying fluid to the at least one inflatable bladder from a tank of fluid stored in the capsule. Inflating the at least one inflatable bladder may comprise supplying fluid via a tether from outside the lumen to the at least one inflatable bladder. Deflating the at least one inflatable bladder may comprise releasing fluid from the at least one inflatable bladder into the lumen.

BRIEF DESCRIPTION OF THE SEVERAL VIEWS OF THE DRAWINGS

The present invention will now be described by way of non-limitative example only, with reference to the accompanying drawings in which.

DETAILED DESCRIPTION

Figure 1:
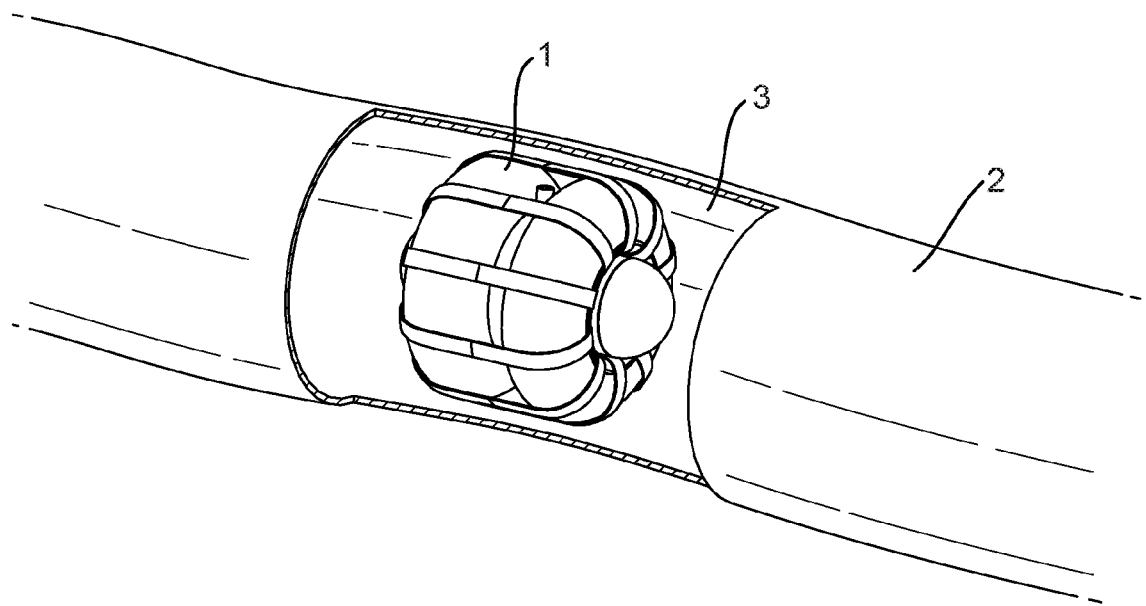
FIG. 1 shows an apparatus for capsule endoscopy according to the present invention inside a lumen.

FIG. 1 shows an apparatus 1 for capsule endoscopy. As shown in FIG. 1, the apparatus 1 can be positioned in the lumen of a tube 2. For example, the tube 2 may be part of the GI tract. However, the apparatus 1 can be used in other tubes inside the body or outside the body (e.g. a pipe). The apparatus 1 is suitable for capsule endoscopy, gastroscopy and colonoscopy.

The apparatus 1 is configured to move through the tube 2 while maintaining contact with at least part of the internal wall 3 of the tube 2. The apparatus 1 can move through the tube 2 by frictional contact with the internal wall 3.

Figure 2:
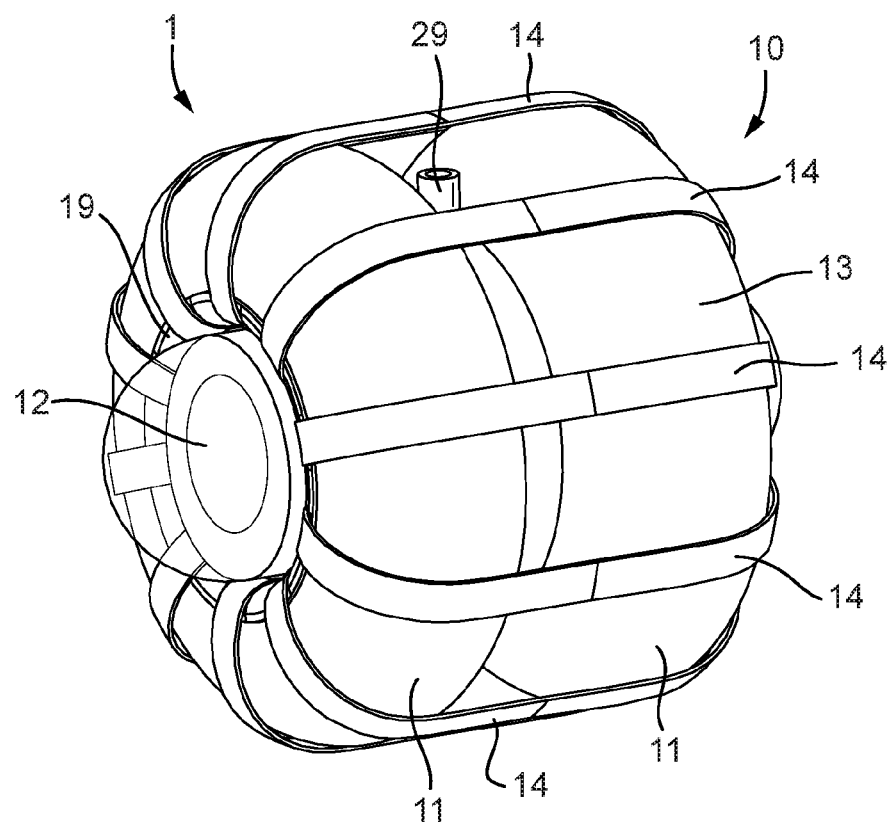
FIG. 2 is an exterior view of an apparatus for capsule endoscopy according to an embodiment of the invention.

FIG. 2 shows an enlarged view of the apparatus 1 shown in FIG. 1. FIG. 2 is a perspective view of the apparatus 1. The apparatus 1 comprises a capsule 10. In the embodiment shown in FIG. 2, the capsule 10 forms the whole of the apparatus 1. However, the apparatus 1 may comprise further components in addition to the capsule 10.

As shown in FIG. 2, in an embodiment the apparatus 1 comprises at least one inflatable bladder 11. FIG. 2 shows an arrangement in which there are two inflatable bladders 11. However, in alternative arrangements there may be only one inflatable bladder 11 or more than two inflatable bladders 11. The invention will be describe below for arrangements that comprise a plurality of inflatable bladders 11. This does not mean that the invention is limited to there being a plurality of bladders 11.

Each inflatable bladder 11 is configured to form a toroid when inflated. The toroid is the shape of a doughnut with a hole in the middle. The toroid has an inner periphery that defines the hole 12, and an outer periphery 13. In the arrangement shown in FIG. 2, the outer periphery 13 has the shape of a circle, which can be seen most clearly when viewing the capsule 10 along the axis that runs through the middle of the hole 12.

As shown in FIG. 2, in an embodiment the capsule 10 comprises a plurality of continuous tracks 14. Each continuous track 14 extends through the hole 12 and around the outer periphery 13 of the inflatable bladders 11. In the arrangement shown in FIG. 2, there are ten continuous tracks 14 provided. The number of continuous tracks 14 is not particularly limited. For example, there may be two, three, four, five, six, seven, eight, nine or more than ten continuous tracks 14.

The continuous tracks 14 are supported by the inflated bladders 11. The inflated bladders 11 force the radially outermost section of the continuous tracks 14 outwards to form external surfaces of the capsule 10. The outward surfaces of the continuous tracks 14 are for pressing against the internal wall 3 of the tube 2. The continuous tracks 14 have a fractional engagement with the internal wall 3. The inflated bladders 11 press the continuous tracks 14 outwards against the internal wall 3.

Figure 3:
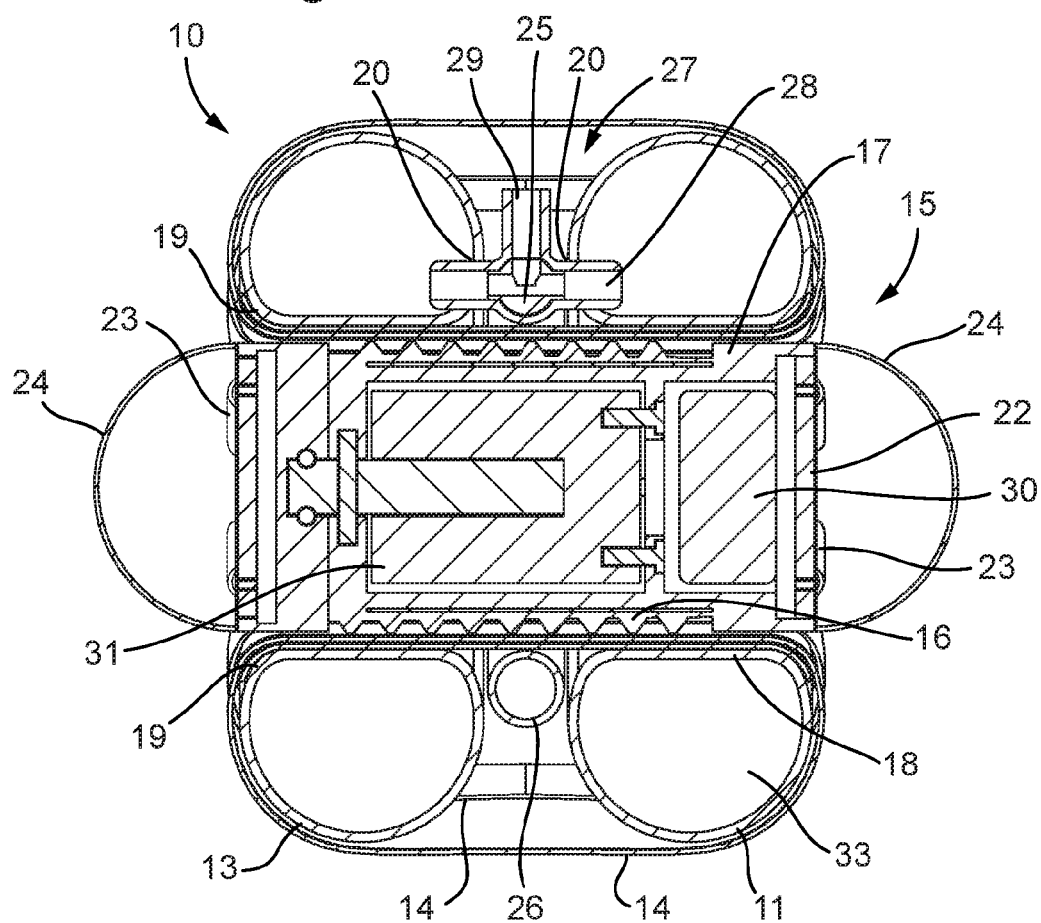
FIG. 3 is a cross-sectional view of the apparatus shown in FIG. 2.

FIG. 3 shows a cross-sectional view of the capsule 10 shown in FIG. 2. As shown in FIG. 3 in an embodiment the capsule 10 comprises a propulsion system 15. The propulsion system 15 is configured to drive the continuous tracks 14. The propulsion system 15 controllably causes the continuous tracks 14 to cycle around the inflated bladders 11.

In an embodiment the capsule 10 is configured such that the continuous tracks 14 slip over the inflatable bladders 11 when the continuous tracks 14 are driven by the propulsion system 15. When the propulsion system 15 drives the continuous tracks 14, the capsule 10 moves through the tube 10. Optionally, the propulsion system 15 is configured to selectably drive the continuous tracks 14 in both directions. This allows the capsule 10 to be driven in both directions along the tube 2.

When the propulsion system 15 drives the continuous tracks 14, the inflated bladders 11 remain fixed in position relative to the main body of the capsule 10. The section of the bladders 11 that forms the inner periphery of the toroid remains the inner periphery of the toroid throughout the movement of the capsule 10. The inner periphery and the outer periphery 13 of the toroid remain substantially stationary relative to each other when the apparatus 1 is in motion. This means that it is possible for the chambers 33 within the bladders 11 to be accessed during use of the apparatus 1. The shape of the cross section of the chamber 33 is not particularly limited. In an embodiment the chamber 33 is a continuous chamber that mobilizes the continuous tracks 14.

By increasing or decreasing the amount of fluid in the chambers 33 inside the bladders 11, the bladders 11 can be controlled to control the outer diameter of the capsule 10 and to control the force with which the continuous tracks 14 push against the internal wall 3 of the tube 2.

The present invention can adapt to the morphology of the GI tract. This is particularly advantageous because the morphology of the GI tract significantly changes from the oral cavity to the anus, both in terms of stiffness and diameter.

The capsule 10 can be controlled so that the continuous tracks 14 exert a force against the internal wall 3. By exerting the force on the internal wall 3, wrinkles or folds in the internal wall 3 can be opened (e.g. stretched) out. This can make it easier to find polyps that would otherwise be hidden in the wrinkles or folds.

As shown in FIG. 3, in an embodiment the capsule 10 comprises at least one valve 20. For example, the arrangement shown in FIG. 3 shows two valves 20. Each valve 20 corresponds to a corresponding inflatable bladder 11. The valve 20 is an inlet/outlet for the chamber 33 of fluid defined by the bladder 11. The valve 20 is configured to receive and expel fluid for inflating and deflating the bladder 11. The chamber 33 contains fluid so that the bladder 11 is at least partially inflated. In a first mode, the valve 20 is controlled to receive fluid into the chamber 33 for inflating the bladder 11. In a second mode, the valve 20 is configured to expel fluid from the chamber 33 so as to deflate the bladder 11.

In an embodiment, the bladder 11 is made of an elastic material. When the chamber 33 receives more fluid, the bladder 11 expands so that the outer diameter of the capsule 10 increases. When the valve 20 expels fluid from the chamber 33, the bladder 11 contracts so as to reduce the outer diameter of the capsule 10.

As shown in FIG. 3, in an embodiment the capsule 10 comprises a controller 22. The controller 22 is configured to control an inflation level of the bladders 11. For example, the controller 22 may control the valves 20 to increase or decrease the amount of fluid in the chambers 33. However, it is not essential for the controller 22 to be provided as part of the capsule 10. In an alternative arrangement, the controller 22 may be positioned outside the tube 2. The apparatus 1 can be remotely controlled. The controller 22 may control the apparatus 1 (e.g. the inflation level of the bladders 11) based on input by a user. Additionally or alternatively, the controller 22 may control the apparatus 1 automatically in response to received measurements (e.g. pressure measurements as will be explained in more detail below).

For sections of the GI tract that are wider or have lower stiffness, the inflation level of the bladders 11 can be increased so that the continuous tracks 14 are pushed further out to the internal wall 3. For sections of the GI tract that are narrower or of higher stiffness, the inflation level of the bladders 11 can be decreased appropriately.

In an embodiment, the apparatus 1 comprises at least one pressure sensor 25. In an embodiment the pressure sensor 25 is configured to measure a pressure in the bladders 11. In an embodiment the pressure sensor 25 is configured to measure a pressure in the tank 26. The pressure sensor 25 can provide pressure feedback to the controller 22. The pressure feedback can be used to estimate the force on the internal wall 3 of the tube 2. In an embodiment, the pressure sensor 25 is configured to provide information about the measured pressure to the controller 22. The controller is configured to control the inflation level based at least partly on the information from the pressure sensor 25.

There may be only one pressure sensor 25. Alternatively, a plurality of pressure sensors 25 (e.g. one for each bladder 11) may be provided. In an embodiment the pressure of each chamber 33 can be independently controlled. The pressure sensor 25 may indicate the controller 22 an increase or decrease in the pressure within the chambers 33. An increase in pressure could indicate that the force on the internal wall 3 has increased. A decrease in pressure in the chambers 33 may indicate a decrease in force on the internal wall 3. Hence, the controller 22 may increase the inflation level of the bladders 11 when there is a decrease in pressure, and decrease the inflation level when there is an increase in pressure in the chambers 33.

Additionally or alternatively, in an embodiment the pressure in the chambers 33 is varied by temperature control. For example, in an embodiment the capsule 10 comprises a heater that heats the chamber 33 in order to increase the pressure in the chamber 33. The heater can be switched off to allow the fluid in the chamber 33 to cool down, thereby decreasing the pressure in the chamber 33.

As explained above, although the continuous tracks 14 revolve during motion of the capsule 10, the bladders 11 do not revolve. This means that the valves 20 that allow access to the chambers 33 can have a fixed position. This makes it easier to increase and decrease the pressure in the chambers 33 by using a flow of fluid into and out from the bladders 11. The apparatus 1 can adapt to the varying conditions throughout the GI tract (or other tube 2 through which the capsule 10 moves).

In an embodiment, the continuous tracks 14 are elastic such that they remain taut around the inflatable bladders 11 over a range of inflation levels. As the bladders 11 are inflated and deflated, the elastic treads remain in tension. This means that the outer surface of the continuous treads 14 can remain in frictional contact with the internal wall 3 even when the conditions (e.g. stiffness and diameter) of the tube 2 changes.

As shown in the Figures, optionally the apparatus 1 comprises at least two inflatable bladders 11, wherein the continuous tracks 14 extend between the at least two inflatable bladders 11. In other words, the apparatus 1 may employ a double-chamber system. By providing two inflatable bladders 11, the continuous tracks 14 retain a substantially straight section between the inflatable bladders 11 over a range of inflation levels. The apparatus 1 can retain a shape similar to a cylinder with fillets at the ends rather, providing a better coupling between the surface of continuous tracks 14 and the internal wall 3 of the tube 2 which has a similar shape. This makes it easier to navigate the GI tract (or other tube 2 through which the capsule 10 moves). In contrast, a system that has only one inflatable structure deforms radially when pressurized, resulting in a more spherical shape. A more spherical shape is more difficult to navigate the GI tract (or other tube 2 through which the capsule 10 moves) which is shaped as a pipe.

Additionally, by providing at least two inflatable bladders 11, the continuous tracks 14 extend are in contact with the inflatable bladders 11 on a smaller surface (compared to a design with only one inflatable structure). The continuous tracks 14 are suspended between the inflatable bladders 11 and only touch the inflatable bladders 11 at the extremities. This reduces friction between the continuous tracks 14 and the inflatable bladders 11. In contrast, a system that has only one inflatable structure results in a higher normal force between the chamber and the belts as pressure is applied on the whole internal surface of the belts. This results in a higher friction force, making it harder for the belt-like structures to slide on the inflatable structure without forcing its rotation.

By not requiring the bladders 11 to revolve, the capsule 10 is easier to manufacture than the endoscopic apparatus disclosed in WO2007/050370A2. In particular, it is not necessary to use complicated or expensive vulcanization methods and tools in order to manufacture the capsule 10. Furthermore, it is not necessary to deal with a revolving valve in order to access the chambers 33 to control their pressure.

As shown in FIG. 3, in an embodiment the capsule 10 comprises a housing 17. The housing 17 may form the main body of the capsule 10. The housing 17 is for supporting at least part of the propulsion system 15.

For example, in an embodiment the propulsion system 15 comprises a motor 31. The motor 31 may be housed within the housing 17. As a further example, in an embodiment the propulsion system 15 comprises a gear 16. The gear 16 may be supportably connected to the housing 17. The motor 31 is configured to provide a driving force to the gear 16. The gear 16 is configured to engage with the continuous tracks 14 so as to drive the continuous tracks 14.

In an embodiment, the gear 16 is a worm gear. In an embodiment, the external side of the continuous tracks (i.e. elastic treads) 14 has a pattern that matches the gear 16. This allows the continuous tracks 14 to be driven directly by the gear 16. However, it is not essential for the continuous tracks 14 to be directly driven by the gear 16. As an alternative, further gear components may be positioned between the motor 31 and the continuous tracks 14.

A low friction coupling is provided between the internal side of the continuous tracks 14 and the external side of the bladders 11. This low friction coupling allows the continuous tracks 14 to slip over the bladders 11 while the capsule 10 is in motion through the tube 2. For example, a coating may be applied to the internal side of the continuous tracks 14 and/or to the external surface of the bladders 11 so as to reduce the friction between the surfaces.

In an embodiment, the inner periphery of the toroid that defines the hole 12 is fixed relative to the housing 17. This means that the position of the inner periphery of the toroid does not move relative to the housing 17. For example, the inner periphery of the toroid may be formed of a section of the bladder 11 that is continuous with the rest of the bladder 11, as shown in FIG. 3. The radially inner side of the bladder 11 does not move relative to the housing 17.

As shown in FIG. 3, in an embodiment the apparatus 10 comprises at least one rigid collar 19. The collar 19 is configured to constrain the continuous tracks 14 from moving circumferentially with respect to the hole 12 formed by the at least one inflatable bladder 11. As shown in FIG. 2, the continuous tracks 14 extend around the collar 19. The collar 19 may be provided with a plurality of grooves, each groove corresponding to a continuous track 14. Each continuous track 14 fits into a correspondingly shaped groove in the collar 19. The grooves help to reduce the possibility of the continuous tracks 14 moving circumferentially. This reduces the possibility of the continuous tracks 14 coming into contact with each other or otherwise bunching up or making the distribution of the continuous tracks 14 around the toroid less even.

As shown in FIG. 3, a collar 19 may be provided at both ends of the capsule 10. The collars 19 may be connected to each other, e.g. as a single integral component. The collars 19 may have a fixed position relative to the housing 17. The grooves in the collar 19 help to guide the elastic treads.

In an embodiment, the propulsion system 15 is configured to drive selectable subsets of the continuous tracks 14. For example, the propulsion system 15 may be switchable between different modes for activating different individual continuous tracks 14 or different groups of continuous tracks 14. For example, in an embodiment one or more mechanical brakes are used to allow the continuous tracks 14 to selectably slip relatively to the gear 16.

By driving a selectable subset of the continuous tracks 14, the orientation and movement of the capsule 10 can be controlled more accurately.

As shown in FIG. 3, in an embodiment the apparatus 1 comprises at least one imaging device 23 for imaging surroundings of the apparatus 1. An imaging device (e.g. a camera) 23 may be provided at each of the front and the back of the capsule 10. The imaging devices 23 make it possible for the interior of the tube 2 to be imaged while moving the capsule 10 through the tube 2. For example, the imaging devices 23 can be used to image polyps in the internal wall of the GI tract.

In an embodiment the apparatus 1 comprises at least one drug delivery system. The drug delivery system is configured to deliver a drug to a target region. The drug delivery system may be remotely controlled. In an embodiment the apparatus 1 comprises at least one tool (other than an imaging device or a drug delivery system). In other words, the same platform can be customized with cameras, drug delivery systems, tools or else if needed.

The capsule 10 can be controlled to activate the continuous tracks 14 on only one side of the capsule 10 (but not activating the continuous tracks 14 on the other side of capsule 10). This causes the capsule 10 to advance along the internal wall 3 on only one side of the capsule 10. This movement results in the orientation of the capsule 10 changing, pointing the imaging devices 23 more directly to the internal wall 3. This type of movement can be used to obtain more desirable views of sections of the internal wall 3, e.g. to find polyps.

In an embodiment, the controller 22 is configured to select a subset of the continuous tracks 14 that are to be driven by the propulsion system 15.

The capsule 10 shown in FIGS. 1-3 can be self-propelled. This means that the capsule 10 has the components necessary to move the capsule 10 through the tube 2. The capsule 10 is untethered. As mentioned above, the capsule 10 may be remote controlled such that the controller 22 could be outside of the tube away from the capsule 10. When the capsule 10 is self-propelled, it needs to be self-sufficient for fluid to inflate the bladders 11 and for power.

As shown in FIG. 3, in an embodiment the capsule 10 comprises a tank 26 of fluid. The tank 26 allows fluid to be stored in the capsule 10. This means that it is not necessary for fluid to be provided from outside of the capsule to the bladders 11. The tank 26 is in controllable fluid communication with the bladders 11 for inflating the bladder 11.

For example, as shown in FIG. 3, in an embodiment the capsule 10 comprises a flow controller 27. The flow controller 27 is for controlling flow or fluid in to and out from the bladders 11. The flow controller 27 is configured to control a flow of fluid out from the tank 26. In an embodiment the flow controller comprises a three-states four-ways valve.

As shown in FIG. 3, in an embodiment the flow controller 27 comprises at least one inflation conduit 28. There may be an inflation conduit 28 provided for each bladder 11. The inflation conduit 28 is for transferring fluid from the tank 26 to the bladder 11. In an embodiment, the flow controller 27 comprises an exhaust conduit 29. The exhaust conduit 29 is for expelling fluid to outside of the capsule 10 (e.g. into the tube 2).

As shown in FIG. 2 and FIG. 3, there may be only one exhaust conduit 29 provided. When it is desired to deflate (i.e. reduce the pressure in) the bladders 11, the flow controller 27 is controlled to allow fluid to flow in the reverse direction through the inflation conduit 28 and then out through the exhaust conduit 29. In an embodiment, the controller 22 is configured to control the flow controller 27.

As shown in FIG. 3, in an embodiment the capsule 10 comprises a power supply 30. The power supply is for supplying power to the propulsion system 15. For example, the power supply may be a battery. The type of battery that can be used is not particularly limited. The power supply 30 may be configured to supply power to the imaging device 23. The power supply 30 may be configured to supply power to the controller 22.

Figure 4:
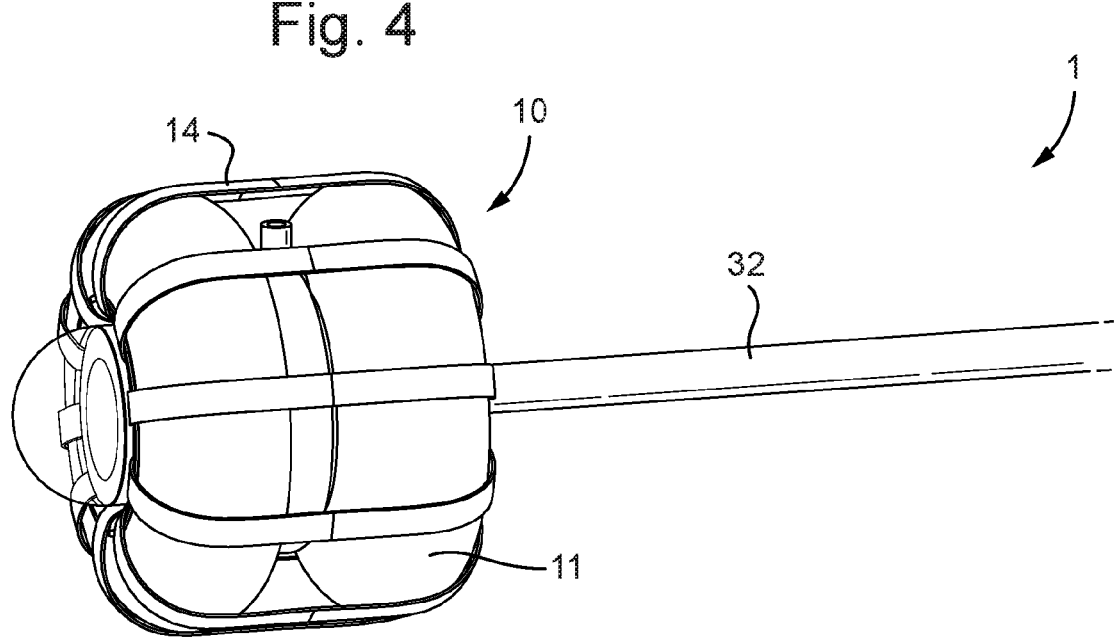
FIG. 4 is a perspective view of an apparatus for capsule endoscopy according to an embodiment of the invention.

It is not essential for the capsule 10 to be self-propelled. FIG. 4 is a perspective view of an apparatus 1 according to an embodiment of the invention. As shown in FIG. 4, in an embodiment the apparatus 1 comprises at least one tether 32. The tether 32 is for supplying power and/or fluid to the capsule 10. The tether 32 may extend from the capsule 10 through the tube 2 to a position outside of the tube 2 (e.g. outside of the body of a patient).

For example, the tether 32 may connect the capsule 10 to a power supply for supplying power to the propulsion system 15 and/or a fluid supply for supplying fluid to the bladders 11 via the tether 32. The tether 32 may comprise at least one electrical wire for supplying an electrical energy to the capsule 10. The tether 32 may comprise at least one pipe for supplying fluid to the bladders 11.

Figure 5:
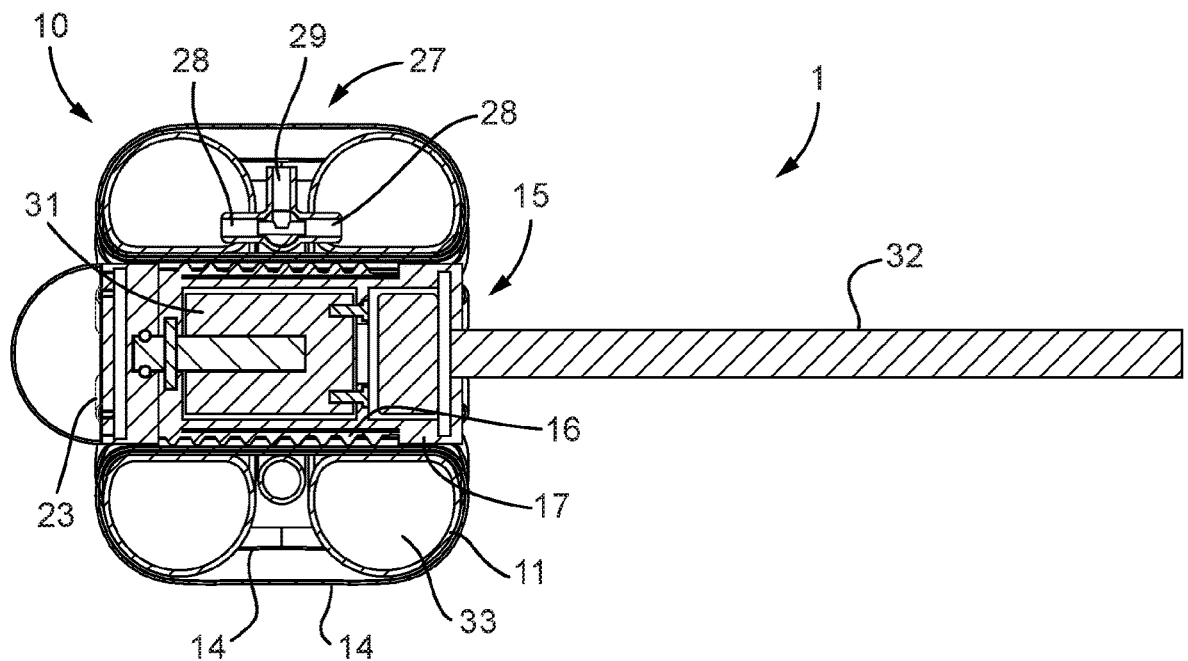
FIG. 5 is a cross-sectional view of the apparatus shown in FIG. 4.

FIG. 5 is a cross-sectional view of the apparatus 1 shown in FIG. 4. A detailed description of the capsule 10 shown in FIGS. 4 and 5 is not given here because the description of the components in relation to FIGS. 2 and 3 applies equally to the components shown in FIGS. 4 and 5.

By providing the tether 32, it is possible to simplify and reduce the size of the capsule 10. In particular, it is not necessary to provide the power supply in the capsule 10. This allows the minimum diameter of the capsule 10 to be reduced. This allows the apparatus 1 to be used in tubes 2 that have a smaller diameter.

When a tether 32 is used to provide fluid for the bladders 11, it may not be necessary to provide the tank 26 describe above. This is because the fluid can be provided through the tether 32. This means that the amount of fluid that can be applied to inflate the bladders 11 is not limited to the amount of fluid that can fit in the tank 26. However, as shown in FIG. 5, the fluid tank 26 can be provided to the capsule 10 even when the tether 32 is also provided.

Figure 6:
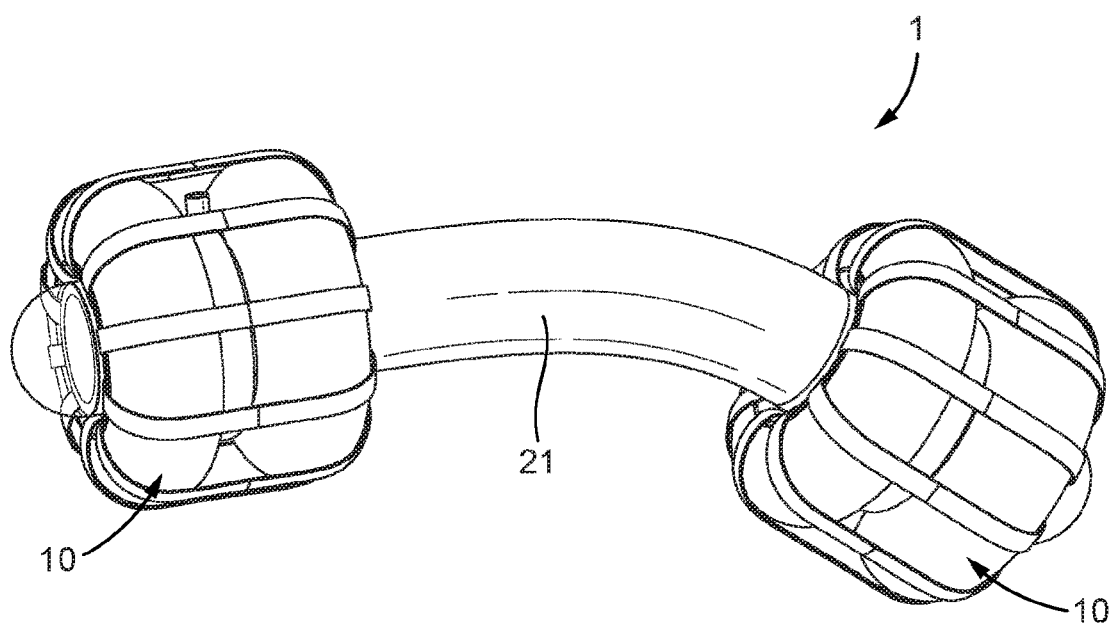
FIG. 6 is a perspective view of an apparatus for capsule endoscopy according to an embodiment of the invention.
Figure 7:
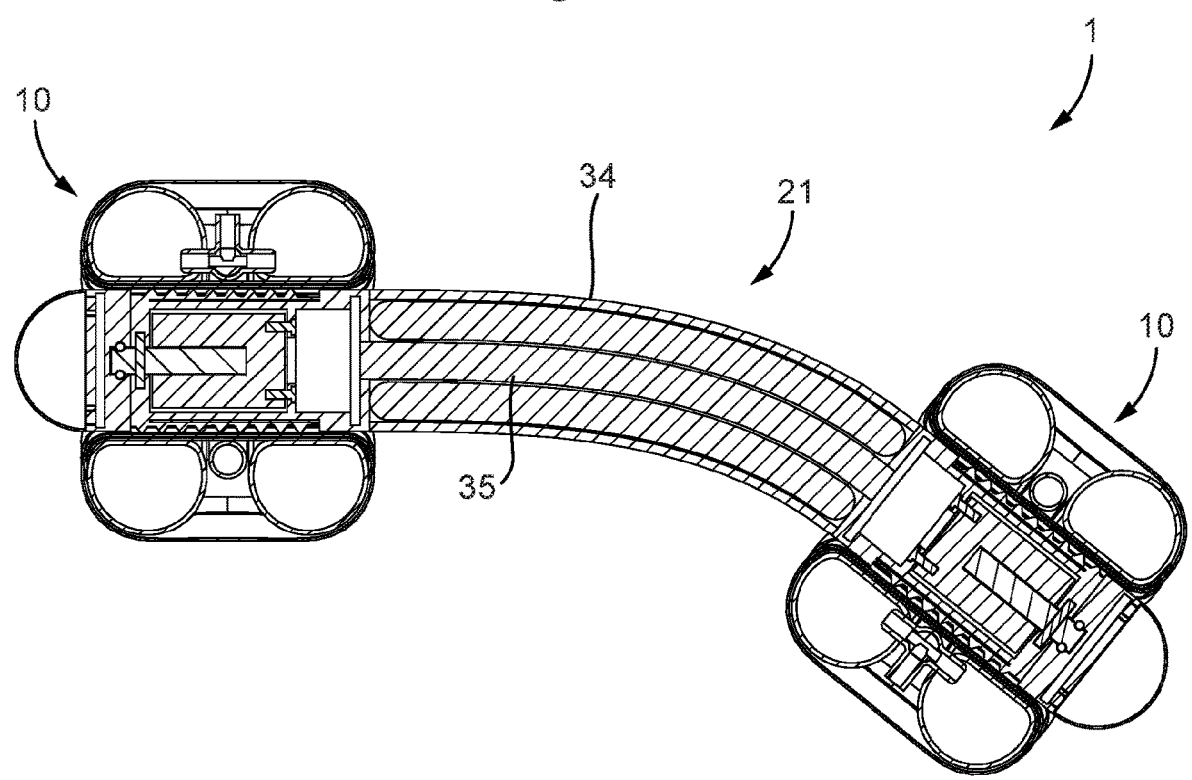
FIG. 7 is cross-sectional view of the apparatus shown in FIG. 6.

FIG. 6 is a perspective view of an apparatus according to a third embodiment of the invention. FIG. 7 is a cross-sectional view of the apparatus 1 shown in FIG. 6. A detailed description of the capsule 10 shown in FIGS. 6 and 7 is not given here because the description of the components in relation to FIGS. 2 and 3 applies equally to the components shown in FIGS. 6 and 7.

As shown in FIGS. 6 and 7, in an embodiment the apparatus 1 comprises at least two capsules 10. The capsules 10 are connected end-to-end by a flexible connector 21. As shown in FIG. 7, in an embodiment the flexible connector 21 comprises an outer sleeve 45 surrounding an inner connector 35.

By providing two capsules 10 connected by a flexible connector 21, the section of the internal wall 3 that is between the two capsules 10 can be stretched out and unfolded. This can reduce wrinkles or folds in the internal wall 3. This can allow any polyps that may be otherwise hidden in folds to be imaged more easily. One or more sensors, e.g. imaging devices may be provided for imaging the section of the internal wall 3 that extends between the capsules 10 of the apparatus 1.

The scale of the apparatus 1 is not particularly limited. In an embodiment, the diameter of the capsule 10 may be at most 50 mm, optionally at most 30 mm, and optionally at most 15 mm (when the bladders 11 are deflated).

The apparatus 1 may be provided with one or more sensors for sensing conditions in the tube 2. As mentioned above, one type of sensor is an imaging device 23. However, other types of sensors may be used, for example a pressure sensor and/or a temperature sensor.

The figures and previous description relate to preferred features by way of illustration only. It should be noted that alternative features of the structures and methods disclosed herein will be readily recognized as possible alternatives. The equipment described above is by way of example only, and it will be appreciated that it may be modified in several different ways while remaining within the scope of the claims.

Features of the different embodiments and arrangements may be combined with each other, except where these are mutually exclusive. For example, although a power supply is not essential for the arrangement shown in FIGS. 4 and 5, a power supply such a battery could be provided for the capsule 10. The power supply could provide a useful back up in case the power supply via the tether 32 fails.

We claim:

1. An apparatus for capsule endoscopy, the apparatus comprising a capsule that comprises:
    at least one inflatable bladder configured to form a toroid having a hole and an outer periphery when inflated;
    a plurality of continuous tracks, each extending through the hole and around the outer periphery of the at least one inflatable bladder;
    a propulsion system configured to drive the continuous tracks; and
    at least one rigid collar configured to constrain the continuous tracks from moving circumferentially with respect to the hole formed by the at least one inflatable bladder;
    wherein the capsule is configured such that a section of the at least one inflatable bladder that forms an inner periphery of the toroid remains the inner periphery of the toroid when the continuous tracks are driven by the propulsion system.

2. The apparatus of claim 1, wherein the capsule is configured such that the continuous tracks slip over the at least one inflatable bladder when driven by the propulsion system.

3. The apparatus of claim 1, wherein the capsule comprises at least one valve corresponding to the at least one inflatable bladder and configured to receive and expel fluid for inflating and deflating the bladder.

4. The apparatus of claim 1, comprising a controller configured to control an inflation level of the at least one inflatable bladder.

5. The apparatus of claim 4, comprising at least one pressure sensor configured to measure a pressure in the at least one inflatable bladder.

6. The apparatus of claim 5, wherein the at least one pressure sensor is configured to provide information about the measured pressure to the controller, and the controller is configured to control the inflation level based at least partly on the information from the at least one pressure sensor.

7. The apparatus of claim 1, wherein the continuous tracks are elastic such that they remain taut around the at least one inflatable bladder over a range of inflation levels of the at least one inflatable bladder.

8. The apparatus of claim 1, the capsule comprising a housing for supporting at least part of the propulsion system, wherein an inner periphery of the toroid that defines the hole is fixed relative to the housing.

9. The apparatus of claim 1, wherein the propulsion system is configured to drive a selectable subset of the continuous tracks.

10. The apparatus of claim 1, comprising at least two inflatable bladders, wherein the continuous tracks extend between the at least two inflatable bladders.

11. The apparatus of claim 1, comprising at least two of said capsule, wherein the at least two capsules are connected end-to-end by a flexible connector.

12. The apparatus of claim 1, comprising at least one imaging device for imaging surroundings of the apparatus.

13. The apparatus of claim 1, wherein the capsule is self-propelled.

14. The apparatus of claim 13, the capsule comprising a tank of fluid stored in the capsule, wherein the tank is in controllable fluid communication with the at least one inflatable bladder for inflating the at least one inflatable bladder.

15. The apparatus of claim 13, the capsule comprising a power supply for supplying power to the propulsion system.

16. The apparatus of claim 15, wherein when the apparatus comprises a controller, the power supply is configured to supply power to the controller.

17. The apparatus of claim 1, comprising at least one tether for supplying power and/or fluid to the capsule.

18. A method of capsule endoscopy, the method comprising:
providing in a lumen an apparatus comprising a capsule that comprises:
at least one inflatable bladder configured to form a toroid having a hole and an outer periphery when inflated;
a plurality of continuous tracks, each extending through the hole and around the outer periphery of the at least one inflatable bladder;
a propulsion system configured to drive the continuous tracks; and
at least one rigid collar configured to constrain the continuous tracks from moving circumferentially with respect to the hole formed by the at least one inflatable bladder; and
driving the continuous tracks with the propulsion system such that the continuous tracks slip over the at least one inflatable bladder and the capsule moves along the lumen.

19. The method of claim 18, comprising:
inflating and/or deflating the at least one inflatable bladder to an inflation level such that the continuous tracks press against a wall defining the lumen;
measuring a pressure in the at least one inflatable bladder; and
controlling the inflation level based at least partly on the measured pressure.

* * * * *